March 6, 1945. B. D. DRAIN Plant Pat. 653

RED RASPBERRY PLANT

Filed Sept. 9, 1943

Inventor
Brooks D. Drain
Attorney
Cameron, Kerkam & Sutton

Patented Mar. 6, 1945 Plant Pat. 653

UNITED STATES PATENT OFFICE

653

RED RASPBERRY PLANT

Brooks D. Drain, Knoxville, Tenn., assignor to The University of Tennessee Research Corporation, Knoxville, Tenn., a corporation of Tennessee Application September 9, 1943, Serial No. 501,688

1 Claim. (Cl. 47—62)

This invention pertains to the asexual reproduction of red raspberry plants, and specifically to the asexual reproduction of a new and distinct variety of red raspberry produced by the artificial pollination of the Lloyd George variety with pollen from the Tennessee Seedling VVF169 (see American Society for Horticultural Science, volume 36, pages 303, 304).

The object of the invention is to produce a new variety of red raspberry plant which possesses better commercial qualities than varieties now in existence, ripening late and which is particularly adapted to the soil and climate of the State of Tennessee.

The new variety produces large crops of large attractive and well flavored berries; larger yields and better quality fruit than Latham which ripens at nearly the same season. Comparable plots at Knoxville, Tennessee, have averaged larger yields than St. Regis, an early ripening variety extensively grown in this section of the United States. All plots of the new variety have been entirely free from mosaic, a disease which has destroyed other varieties growing near by.

Figure 1:
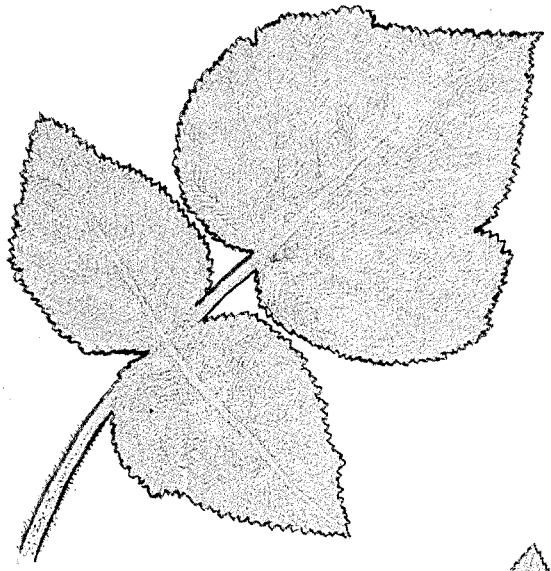
Figure 3:
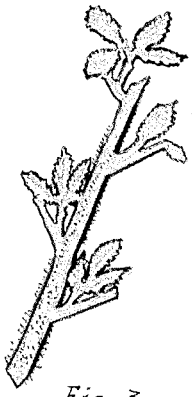
Figure 2:
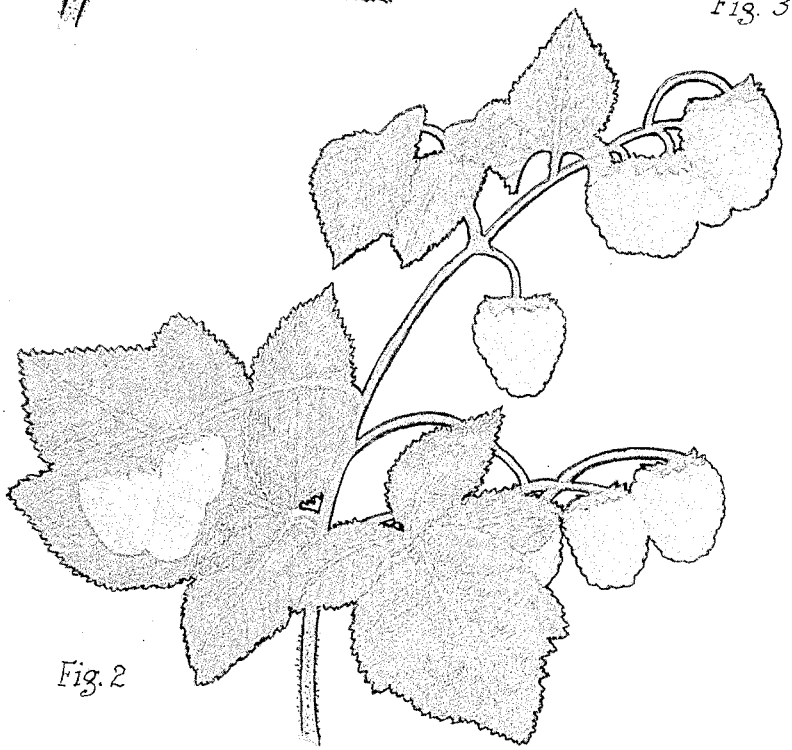

In the accompanying drawing Fig. 1 is a view of a leaf of the plant showing its color and other characteristics; Fig. 2 is a view of a fruiting cluster of the plant showing ripe and green berries; and Fig. 3 is a view of a short piece of cane as it appears in the dormant season.

In producing the plant of the present invention, Tennessee Seedling VVF169 was secured by placing the pollen of Viking red raspberry in the blossom of the Van Fleet plant, the pollen producing parts of the blossom of the Van Fleet having first been removed. The pollenated blossom was then protected so that it could not receive pollen from any other plant, and was allowed to develop into fruit. The seeds from this fruit were then planted and permitted to sprout, and after the plants had grown to sufficient size, they were allowed to fruit in the field. Tennessee Seedling VVF169 was selected from a large number of plants because of its health, vigor, productiveness and desirable fruit characters. This process was then repeated using the Lloyd George plant as the maternal parent and Tennessee Seedling VVF169 as the paternal parent. At about the time that these progenies were fruiting in the field, each plant and its vegetatively developed sucker plants were examined for freedom from insects and diseases and for desirable growth habits. The fruit was also examined and tasted for desirable fruit characteristics. The best among a large number of seedlings was then selected, saved and propagated asexually, using either sucker plants, root cuttings or rooted leaf cuttings to produce the plant of the present invention. All plants which are now growing including the one from which the accompanying drawing was made have come from this original seedling.

The new variety does not resemble either of its parents being larger fruited and less vigorous than Tennessee Seedling VVF169. Lloyd George is a variety imported from England and makes a weak and unsatisfactory growth in Tennessee soil and climate in contrast to the new variety which thrives under these conditions.

One vigorous mother plant of the new variety will usually produce a few but not many sucker plants. I have resorted to leaf cuttings taken in late summer to increase the supply of plants. Root cuttings have been used in mid-winter with some success. The plants are tall, vigorous and upright. The canes are stocky, green in color and tinged with purple in late summer. The foliage of the plant is medium size, medium green in color, with dull roughened upper surface and whitish lower surface. Some leaf spot and anthracnose has been noted, but the foliage is comparatively healthy.

The berries produced by this plant are large in size and firm. Their shape is conic with length and width about equal. The surface of the berry is medium red in color, glossy and attractive and with a medium amount of bloom. The individual parts of the berry are strongly coherent. The fruit is sub-acid and very good in flavor. Other characteristics of the new red raspberry are as follows:

Plants: Tall; upright; vigorous.

*Propagated by suckers and cuttings.*—Hardy; very productive.

*Suckers.*—Few.

*Canes.*—Stocky; Green, with Purple in late summer; dull; pubescent. *Spines or prickles*—slender; straight; sharp; medium in number. Distribution—few toward the base and many toward the tip. Color—Reddish.

*Leaflets.*—Number usually 5; medium in size; ovate in shape. Upper surface—Medium Green in color; dull; roughened. Lower surface—Whitish. Tomentose. Margin—crenate; uneven; double series; glandular. Petiole—medium in length; thick; prickly; pubescent.

*Flowers.*—Late.

Fruit: Season late.

*Date of ripening.*—Started June 14, 1940, at Knoxville, Tennessee; ended July 24, 1940, at Knoxville, Tennessee.

*Length of season.*—About 40 days.

*Borne how.*—Leafy cluster with 7 berries usually.

*Keeping quality.*—Good.

*Shipping quality.*—Excellent.

*Picking quality.*—Good.

*Adherence.*—Strong; large; uniform; retains size through season; regular; long; roundish conic.

*Bloom.*—Medium in amount.

*Styles.*—Usually present.

*Drupes.*—Small numerous. Coherence—strong. Medium Red color, R4/10 to R4/14, Munsell Book of Color, published by Munsell Color Co. Inc., 1929. Glossy; medium juicy; tender; firm; not seedy; subacid; springhtly; high-flavored; aromatic. Quality—best.

*Use.*—Dessert; kitchen; market; home.

*Desirability.*—Excellent commercial variety.

*Remarks.*—Slow propagation may seriously handicap this variety.

*Classification.*—Red raspberry.

What is claimed is:

A red raspberry plant variety substantially as herein disclosed which is characterized by late ripening, producing one crop in a given season, starting growth late in the spring, and which is particularly adapted to the soil and climate of the State of Tennessee.

BROOKS D. DRAIN.